United States Patent [19]

Lozano et al.

[11] 4,010,872

[45] Mar. 8, 1977

[54] OXIDATION HAIR DYE IN A PLURAL-FLUIDS DISPENSING PACKAGE

[75] Inventors: David S. Lozano; Samuel B. Prussin, both of Los Angeles, Calif.

[73] Assignee: Dart Industries Inc., Los Angeles, Calif.

[22] Filed: Mar. 13, 1972

[21] Appl. No.: 234,357

Related U.S. Application Data

[63] Continuation of Ser. No. 799,941, Feb. 17, 1969, abandoned, which is a continuation-in-part of Ser. No. 755,823, Aug. 28, 1968, abandoned.

[52] U.S. Cl. .................................. 222/94; 8/10.2; 8/11; 8/32; 8/79; 8/111; 206/216; 206/219; 222/136; 222/192; 424/DIG. 1; 424/DIG. 3; 424/47; 424/62; 424/73

[51] Int. Cl.² ............................................ B65D 35/22

[58] Field of Search ................... 8/10.2, 32, 11, 79; 424/47; 222/192, 136, 94; 206/219, 216, 84

[56] References Cited

UNITED STATES PATENTS

| 2,774,355 | 12/1956 | Bell ................................ 424/71 X |
|---|---|---|
| 2,973,883 | 3/1961 | Modderno ........................ 222/94 |
| 3,055,834 | 9/1962 | Charle et al. .................... 424/47 X |
| 3,194,734 | 7/1965 | Seemuller et al. ................ 8/10.2 |
| 3,241,722 | 3/1966 | Nissen et al. .................... 222/136 |
| 3,255,926 | 6/1966 | Modderno ........................ 222/94 X |
| 3,325,056 | 6/1967 | Lewis ............................ 222/94 |
| 3,337,411 | 8/1967 | Wilmsmann et al. .............. 8/10.2 |
| 3,341,418 | 9/1967 | Moses et al. .................... 424/47 X |
| 3,415,608 | 12/1968 | Tucker ............................ 8/10.2 |
| 3,455,489 | 7/1969 | Meshberg ........................ 222/94 |
| 3,488,287 | 1/1970 | Seglin et al. .................... 424/73 X |

*Primary Examiner*—Albert T. Meyers
*Assistant Examiner*—Vera C. Clarke
*Attorney, Agent, or Firm*—Kenneth J. Hovet

[57] ABSTRACT

Packages are described wherein two compositions are maintained isolated from each other within a container, the first composition comprising an oxidation hair dye and the other comprising hydrogen peroxide. The container is fitted with valve means which communicate with each composition, actuation of the valve means resulting in mixing of portions of each composition and dispensing of the mixture as a hair dye. Through the addition of a reducing agent or a hydrogen peroxide decomposition catalyst to the first composition, the hair dye can be dispensed in a warmed state. A process for packaging of plural fluids to insure uniform dispensing in which one is a foamable liquid is described wherein the foamable liquid is placed within an inner compartment within a container separated from the remainder of the container by a movable wall and a pressurized fluid is placed inside the container outside the inner compartment.

1 Claim, No Drawings

OXIDATION HAIR DYE IN A PLURAL-FLUIDS DISPENSING PACKAGE

This application is a continuation of application Ser. No. 799,941, filed Feb. 17, 1969, now abandoned which is a continuation-in-part of our application entitled "Hair Dye Dispensing Package and Plural Fluids Packaging and Dispensing Process Therefor" Ser. No. 755,823, filed Aug. 28, 1968 now abandoned.

This invention relates to packages adapted to storage of plural fluids which upon dispensing combine to form a desired composition, for example a composition useful for dyeing human hair, and to a process for packaging and dispensing plural fluids.

Chemical compounds which are capable of being oxidized to yield colored oxidation products have been widely used by cosmetic chemists in developing hair dyeing products, such compounds being generally referred to as oxidation hair dyes. The most common of such products are based upon aromatic compounds which are capable in an alkaline medium of rapid oxidation by an oxidizing agent such as hydrogen peroxide to yield colored by-products having color shades which have a high degree of consumer appeal on application to human hair. Products based upon this concept are customarily packaged with the alkaline system containing dye chemical and hydrogen peroxide in separate packages which are mixed prior to use. This represents a relatively messy and cumbersome operation for the consumer and there has long been a need for a package in which the mixing of the ingredients is carried out automatically and where the final mixture can be dispensed directly to the hair.

There has been considerable interest expressed in recent years by workers in the art of cosmetic packaging in the concept of packages adapted to store at least two compositions which are maintained isolated from each other within the package and which combine only at the moment of dispensing. There are many use applications for such plural dispensing packages, including, for example hot foam products such as shaving foams, cleansing foams, hair dye foams and the like. Mixing of the two compositions during the dispensing operation results in a chemical reaction with liberation of heat. Compositions adapted to form products of this nature, for example shaving soap formulations, are notorious foam-formers when shaken. As the contents of such a package are exhausted during normal use, shaking of the container prior to use results in the conversion of a constantly increasing proportion of the compositions into foam with resulting decrease in density of the liquid phase. This contributes to incorrect proportioning and, as a result, an unsatisfactory product. There has, therefore, long been a need for a package adapted to dispense plural fluids, one of which is a foamable composition when shaken.

The invention sought to be patented in its first product aspect resides in the concept of a package with means to maintain two compositions therein isolated from each other, one of said compositions comprising an oxidation hair dye and the other of said compositions comprising hydrogen peroxide; and valve means communicating with each of said compositions whereby the application of pressure to the compositions and actuation of the valve means results in the mixing of portions of each of said compositions and dispensing of the mixture from the package in a form suitable for direct application to human hair. In accordance with further features of the first product aspect of this invention, the composition comprising an oxidation hair dye can also include a reducing agent or a catalyst capable of reacting with or promoting the decomposition of hydrogen peroxide to liberate heat such that the dye mixture will be dispensed from the package in a warmed state.

The invention sought to be patented in its second product aspect resides in the concept of a package with means to maintain two liquids, one of which is foamable, isolated from each other which comprises a pressure-tight container with an inner compartment separated from the main body portion of the container by a movable wall operable by a pressure differential, the foamable liquid being packaged within the inner compartment and the other liquid being maintained within the container outside the compartment, means to apply pressure to the container and valve means communicating with each liquid whereby actuation of the valve means results in mixing of portions of each liquid and dispensing of the mixture from the package in aerosol form, constant proportioning of the liquids being maintained throughout the dispensing life of the package.

The invention sought to be patented in its process aspect resides in the concept of a method for packaging and dispensing a plurality of fluids including a foamable liquid and a pressurized liquid which comprises placing the foamable liquid in an inner compartment within a container which is separated from the main body portion of the container by a movable wall and placing a pressurized fluid in the container outside the inner compartment whereby the pressurized fluid acts through the movable wall to pressurize the foamable liquid and thereby provides a liquid column in said inner compartment without head space, said container being fitted with a valve mechanism communicating with both the inner compartment and the space within the container surrounding the inner compartment; and dispensing said fluids concurrently from both compartments by actuation of said valve mechanism whereby accurately proportioned delivery of the two liquids relative to each other is effected through the maintenance of the foamable liquid within the inner compartment throughout the dispensing operation as a liquid column without head space.

Other aspects of the invention will become apparent from the following detailed description and the appended claims.

The manner and process of making and using the invention will now be described generally so as to enable one skilled in the art of cosmetic chemistry to make and use the same as follows:

Packages within the scope of the first product aspect of the present invention are in the form of a container filled with two compositions which are maintained isolated from each other. One of these compositions comprises an oxidation hair dye. As used herein, the term "oxidation hair dye" means any chemical capable of reacting in an alkaline medium with hdyrogen peroxide to yield a colored material which is adapted to the safe application to human hair to change its color. Typical chemicals within the scope of the term "oxidation hair dye" aromatic nitro and/or amino compounds such as o- and p-phenylenediamine, 2,4-diaminoanisol, p- and m-toluylene diamine, nitro substituted o-, m- and p-phenylenediamine, o- and p-aminophenol and nitro-substituted derivatives thereof, p-aminodiphenyl amine, p-aminodimethyl aniline, p-aminocresol and the like. The term "oxidation hair dye" embraces a dyeing system containing mixtures of compounds as above described including systems including conventional modifiers such as resorcinol, pyrogallol, pyrocatechin, 2-naphthol and the like. The entire subject of oxidation hair dyes has been extensively described in the literature, for example in a series of articles entitled "Technology of Modern Oxidation Hair Dyes", appearing on pages 25–28, 35–37 and 47–50 in, respectively, the July, August and September (1956) issues of American Perfumer and Aromatics.

As described above, an oxidation hair dye is identified as a chemical capable of reacting in an alkaline medium with hydrogen peroxide to yield a colored material adapted to the safe application to human hair to change its color and/or to maintain its present color. Accordingly, the composition comprising oxidation hair dye in the preparation of packages within the scope of the present invention must include an alkaline substance adapted to produce a pH in the range of about 8.5 to about 10.0 in the final mixture as dispensed from the package. In accordance with normal procedures in the art of hair dyeing, this alkaline substance can be ammonia, or ammonium hydroxide which is the form in which ammonia exists in an aqueous system. Lower alkyl and lower alkanol substituted ammonium hydroxides in which the lower alkyl or lower alkanol portion contains 1 or 2 carbon atoms, for example tetramethyl ammonium hydroxide, tetraethyl ammonium hydroxide and tetraethanol ammonium hydroxide, and corresponding substituted sufonium hydroxides, for example trimethylsulfonium hydroxide, are the full equivalents of ammonia (or ammonium hydroxide) in the invention.

Alternately, the alkaline substance can be a lower alkanolamine containing 2 to 4 carbon atoms, for example, monoisopropanolamine, monoethanolamine, monobutanolamine, and the like.

The other composition, which is maintained in the package isolated from the oxidation hair dye composition, comprises hydrogen peroxide. In the case of packages which dispense products at room temperature, the amount of hydrogen peroxide will be that reactable with the oxidation hair dye ingredient contained within the package. In accordance with other aspects of this invention where dispensing of a warmed product is desired, an additional amount of hydrogen peroxide will be present as described hereinafter.

The composition comprising hydrogen peroxide will also include conventional stabilizers and preservatives for hydrogen peroxide and will, in addition, include an acid ingredient, for example phosphoric acid, in an amount sufficient to impart an acidic pH to the system to effectuate optimum stability of the hydrogen peroxide.

In the case of the dispensing of warmed compositions, heat can be generated either through chemical reduction of hydrogen peroxide by a reducing agent or by catalytic decomposition with a decomposition catalyst. The reducing agent or the catalyst is present in the composition comprising the oxidation hair dye ingredient. Useful reducing agents including sulfur dioxide and salts derived therefrom such as alkali metal sulfites and bi-sulfites, thiourea, 1-phenyl-2-thiobarbituric acid and its derivatives as described in U.S. Pat. No. 3,341,418, alkali metal sulfides, alkali metal thiosulfates, and the like. It is essential that any reducing agent used in the preparation of packages in accordance with this invention be fully compatible with and stable in the presence of the oxidation hair dye ingredient. Alternately, heat can be generated by the catalytic decomposition of hydrogen peroxide, a reaction which liberates heat with the simultaneous formation of water and oxygen gas. Many materials are well known in the art for catalyzing such decomposition, for example, metals such as silver, lead, iron, chromium, bismuth, copper, titanium, molybdenum and silicon, oxides and salts thereof, activated carbon, enzymatic systems such as catalase, and the like. The particular catalyst used must be stable in the presence of the oxidation hair dye ingredient and, in addition, must not catalyze the decomposition of such ingredient. It is also within the scope of the invention that a combination of both methods of heat generation be employed.

The relative proportions of hydrogen peroxide to oxidation hair dye in packages of this invention where a warmed composition is to be dispensed must be such that there is, first, sufficient hydrogen peroxide to react with the oxidation hair dye ingredient to cause the desired oxidation and, second, an additional increment of hydrogen peroxide which, upon reduction with reducing agent or decomposition with catalyst, will liberate the desired amount of heat to result in a meaningful temperature rise upon dispensing.

As described above, the two compositions are maintained isolated from each other within a container. Such a container is constructed of rigid or flexible material depending upon the pressurization means to be utilized for dispensing. A collapsible container formed of plastic or metal is used where pressurization is effected manually by squeezing. In accordance with a preferred embodiment of this invention, self-pressurization is employed through use of a liquefied propellant gas within the container in either or both of the isolated compositions and, in this case, a pressure-tight container having sufficient wall strength to withstand the propellant pressure is employed. The container can be formed of a wide class of materials used in the art of aerosol packaging such as glass, rigid plastics and metal. Such propellants must be of such a nature that they are compatible with the compositions in which they are included. Such propellants should have a vapor pressure of approximately 12 to 85 pounds per square inch gauge at 70° F using as propellants saturated aliphatic hydrocarbons such as propane, butane, isobutane and the like, and/or chlorofluoralkanes containing not more than two carbon atoms and at least one fluorine atom having the desired vapor pressure for use in the invention. Propellant gases such as nitrogen, carbon dioxide or nitrous oxide or liquefied propellants such as dimethyl ether with a high degree of water solubility may also be used as pressurization means. Mixed propellant systems can also be employed, for example a mixture of dimethyl ether and a chlorofluoroalkane or hydrocarbon, or a hydrocarbon or chlorofluoroalkane in combination with a gas such as nitrogen, carbon dioxide or nitrous oxide. In addition, a modifier to adjust solubility and volatility of the propellant, such as pentane, can be present. A propellant system based upon pentane and a liquefied propellant such as the chlorofluorocarbons has been found to impart a delayed foaming of the dispensed hair dye. That is, the product emerges in the liquid state which is ideal for penetration to all hair on the head and then after a lag time of several seconds, forms a stable foam with dimensional stability, a form ideally adapted to holding and distributing the product throughout the hair. Other lower hydrocarbons and organic modifiers of like properties are the full equivalents of pentane for use in the invention.

The two compositions, formulated as described above, are packaged with a container in such a way as to remain isolated from each other. Valve means are provided to communicate with each composition such that, upon actuation of the valve means, a quantity of each composition is mixed and the resulting mixture is dispensed from the package. It is apparent that the concentration of the respective ingredients must be adjusted in relation to the proportioning properties of the valve means such that a proper mixture of the two compositions based upon the desired end use results from actuation of the valve means.

There are many different ways in which the final package can be constructed in accordance with the first product aspect of this invention which will influence the selection of appropriate valve means and the means selected for pressurization. Several such ways are discussed hereinafter.

The package can be constructed in the form of a two-chambered container, separated by a rigid wall, with each chamber fitted with a valve leading to a common discharge conduit. Such a structure is illustrated in U.S. Pat. No. 2,941,696 and with this type of package both compositions are pressurized. Alternately, structure as illustrated in U.S. Pat. No. 3,295,727 can be employed in which case one of the compositions is pressurized and is present in the body portion of the container with the second composition in the illustrated chamber surrounding the dip tube. The vapor pressure of the first composition bears upon the second composition in this structure and both are dispensed upon valve actuation. U.S. Pat. No. 3,272,389 illustrates another form of package construction useful in the invention. In this structure, venturi action of the pressurized composition within the container provides the motive force for dispensing the second composition.

A particularly desirable form of package for use in accordance with the invention in its first product aspect and the package form of packages constructed in accordance with the second product aspect of this invention is to utilize a package having two compartments in which the two compositions are packaged within a pressure-tight container, the compartments being separated by a movable wall actuatable upon a pressure differential between the two compartments when the valve means affixed to the container are actuated. The composition within the container outside the movable wall is pressurized. In such a system, the movable wall can be in the form of a movable piston, for example, as illustrated in U.S. Pat. No. 3,217,936, or in the form of a collapsible bag as illustrated in U.S. Pat. No. 2,973,883.

The disclosure of all of the aforementioned patents are incorporated by reference herein for illustrative purposes to the same extent as if set forth at length herein. It is to be understood that such patents are merely illustrative of various means to package the two compositions of this invention within a container and to dispense portions of both compositions to insure mixing and dispensing upon actuation of the valve means.

As stated hereinabove, a particular desirable form of package in accordance with the first product aspect of this invention is a two-compartmented package in which the compartments are separated by a movable wall, for example, in the form of a piston or a collapsible bag. While in the case of this type of package, as with other packages as above described, each composition can be included in either compartment, it has been found that optimum results in terms of dispensing a hair dye with reproducible dyeing effect from actuation to actuation is effected by packaging the oxidation hair dye composition within the inner compartment of the container separated from the main body portion of the container by a movable wall. As will be recognized by one of normal skill in the art, a liquid composition packaged within a collapsible bag or within a chamber separated from another compartment by a piston will be liquid-full with no head space throughout the dispensing life of the package when the space within the package outside the bag or piston is pressurized. It has been observed that oxidation hair dye formulations are unusually susceptible to foam production upon shaking. Inasmuch as consumers are in the habit of shaking aerosol containers before use, a composition susceptible to foam formation in a compartment with vapor head space will produce foam. This foam results in a stable gas phase within the liquid and by conversion of a portion of the liquid into a stable froth above the liquid, both factors contributing to a reduction in the density of the liquid phase. The effect becomes more pronounced as the head space increases. In accurate codispensing of two liquids through a valve, proportioning of the two liquids is necessary to form a proper mixture. In the devices described hereinabove, such proportioning is attained by maintaining uniform cross-sectional areas for flow of each liquid. Flow rates will vary through the uniform cross-sectional areas if one of the liquids is in a foamed condition and the other is in a liquid state. The problem is particularly serious if one of the liquids becomes more highly foamed as the dispensing process continues in that non-uniform proportioning results and the resulting mixture of liquids will not meet the critical standards for chemical reaction. It has been found that if the oxidation hair dye-containing composition, which is susceptible to foam formation, is packaged within a compartment having no head space, it is apparent that foaming is effectively eliminated and uniform proportioning is attained throughout the dispensing life of the package. Accordingly, the particularly effective package in accordance with this invention in its first product aspect is that in which the two compartments are separated by a movable wall and wherein the oxidation hair dye composition is packaged in the inner compartment.

As has been described hereinabove, the concept of a dual-compartmented container where the two compartments are separated by a movable wall is a particularly effective package for hair dye products in accordance with the first product aspect of this invention. Such a dual-compartmented container is the package form for products in accordance with the second product aspect of this invention. In addition to oxidation hair dye formulations, other products which are amenable to co-dispensing, for example to produce warmed products based upon an oxidation-reduction reaction, including shaving lather, cleansing foams and the like and such formulations are notorious foamers when shaken. In accordance with this invention, a package for co-dispensing two liquids, one of which is foamable, is constructed with a container having two compartments, the inner being separated from the outer by a movable wall. The foamable liquid is placed in the inner compartment and the second liquid which is pressurized is placed in the outer compartment. Pressure acting upon the movable wall causes the liquid within the inner compartment to fill it completely with no free or head space. Shaking such a package yields no foam and throughout the dispensing life of the package, the respective densities of each liquid remain constant, insuring uniform proportioning of the liquids resulting in a proper mixture being formed.

Packages of this invention are filled by conventional means. Where pressurization is brought about by a liquefied propellant included in either or both compositions, filling can be by either pressure- or cold-filling techniques.

This invention has been described with specific reference to hydrogen peroxide as the agent which oxidizes the hair dye and, in the case of dispensing a warmed composition, is subjected to catalytic decomposition or reduction to liberate heat. It is apparent that other substances of like properties can also be used, such as derivatives of hydrogen peroxide, for example, urea hydrogen peroxide and other organic and inorganic peroxides, as well as perborates and persulfates, all of which are the full equivalents to hydrogen peroxide in the preparation of packages within the scope of the invention.

The two compositions may be formulated with added ingredients conventional in cosmetic products. For example humectants, fragrances, surfactants and emulsifiers to yield a product dispensed from the package with the desired degree of cosmetic elegance for optimum consumer appeal. In the case of oxidation hair dye products, the use of added surfactants of the class conventionally utilized in shampoos permits the creation of hair dyes of the "shampoo-in" type. The hydrogen peroxide compositions may contain emulsifiers where insoluble propellants are used and a readily reconstitutable emulsion is desired. Alternately, with inert gas pressurization, soluble propellants, or a two liquid phase system, the hydrogen peroxide composition can consist solely of an aqueous acid solution of hydrogen peroxide with an antioxidant.

The best mode contemplated by the inventors for carrying out their invention will now be set forth as follows:

EXAMPLE I

The following compositions are utilized to prepare a package of the form illustrated in U.S. Pat. No. 2,973,883

| A. Hydrogen Peroxide Composition | Parts by Weight |
|---|---|
| Acetophenetidin | 0.04 |
| Polyoxyethylene (2) stearyl ether | 2.02 |
| Polyoxyethylene (20) stearyl ether | 1.73 |
| Cetyl alcohol | 1.00 |
| Hydrogen Peroxide (35% strength) | 17.00 |
| Phosphoric Acid (10% strength) | 0.20* |
| Water, deionized, q.s. | 100.00 |

*Quantity adjusted to attain pH of about 3.75.

B. Oxidation Hair Dye Composition (light auburn shade)

| | |
|---|---|
| o Aminophenol | 0.50 |
| Pyrogallol | 0.25 |
| Resorcinol | 0.20 |
| o-Nitro-p-phenylenediamine | 0.70 |
| Oleic acid | 25.00 |
| Propylene Glycol | 14.00 |
| Butylhydroxyanisole | 0.10 |
| Isopropanol | 10.00 |
| Polyoxyethylene (4) lauryl ether | 5.00 |

-continued

| | |
|---|---|
| Polyoxyethylene (23) lauryl ether | 5.00 |
| Ethoxylated (25) lanolin alcohol ether | 1.00 |
| Lecithin | 1.25 |
| Disodium ethylenediamine tetraacetate | 0.10 |
| Ammonium hydroxide (28% strength) | 15.00 |
| Perfume | Trace |
| Water, deionized q.s. to | 100.00 |

Fill 96 parts by weight of Composition A into a pressure-tight container. Fill a collapsible container having a diameter smaller than the opening in the pressure-tight container with 100 parts by weight of Composition B. Insert collapsible container and affix valve means to communicate individually with the two compositions, the valve means being constructed such that actuation causes flow of Compositions A and B in the relative proportions of 1:1. Pressurize container with 4 parts by weight of a mixture of 84% isobutane -16% propane. Actuation of the valve means results in the mixing of portions of the two compositions to yield a hair dye which is dispensed at room temperature in a form ideally suited for hair dyeing purposes.

The following examples are illustrative of the preparation of packages in accordance with other embodiments of this invention:

EXAMPLE II

The following compositions are utilized to prepare a package of the form illustrated in U.S. Pat. No. 2,973,883:

A. Hydrogen Peroxide Composition

The composition is formulated as in Example I except that 30.00 parts of hydrogen peroxide (35% strength) are used.

B. Oxidation Hair Dye Composition (lt. auburn shade)

The composition is formulated as in Example I except that the ammonium hydroxide is increased to 19.14 parts and the following additional ingredients are added:

Sodium Thiosulfate 4.06 parts by weight
Sodium Molybdate Dihydrate 0.05 parts by weight The compositions are packaged and the package is pressurized as described in Example I. Actuation of the valve means results in the mixing of portions of the two compositions to yield a hair dye which is dispensed in a warmed state in a form ideally suited for hair dyeing purposes.

EXAMPLE III

The following compositions are utilized to prepare a package of the form illustrated in U.S. Pat. No. 2,973,883:

A. Hydrogen Peroxide Composition

The composition is formulated as in Example I.

B. Oxidation Hair Dye Composition (lt. auburn shade)

The composition is formulated as in Example I except that the ammonium hydroxide is replaced by 19.14 parts by weight of monoisopropanolamine.

The compositions are packaged and the package is pressurized as described in Example I. Actuation of the valve means results in the mixing of portions of the two compositions to yield a hair dye which is dispensed at room temperature in a form ideally suited for hair dyeing purposes.

EXAMPLE IV

The following compositions are utilized to prepare a package of the form illustrated in U.S. Pat. No. 2,973,883:

A. Hydrogen Peroxide Composition

The composition is formulated as in Example II.

B. Oxidation Hair Dye Composition (light auburn shade)

The composition is formulated as in Example II except that the ammonium hydroxide is replaced by 22.0 parts by weight of monoisopropanolamine.

The compositions are packaged and the package is pressurized as described in Example I. Actuation of the valve means results in the mixing of portions of the two compositions to yield a hair dye which is dispensed in a warmed state in a form ideally suited for hair dyeing purposes.

EXAMPLE V

The following compositions are utilized to prepare a package of the form illustrated in U.S. Pat. No. 2,973,883 for the purpose of dispensing a hair dye in a warmed state of the shampoo-in type.

| A. | Hydrogen Peroxide Composition | Parts by Weight | |
|---|---|---|---|
| | Polyoxyethylene (2) stearyl cetyl ether | 2.00 | |
| | Cetyl Alcohol | 3.00 | |
| | Acetophenetidin | 0.04 | |
| | Ethylenediamine tetra-Acetate tetra sodium | 0.10 | |
| | Polyoxyethylene (20) Stearyl Alcohol ether | 1.50 | |
| | Sodium lauryl ether sulfate (27%) | 10.00 | |
| | H₂O₂ (30%) | 33.00 | |
| | 10% solution of H₃PO₄ (85%) | 0.57 | ml |
| | Water, deionized q.s. | 100.00 | |
| B. | Oxidation Hair Dye Composition | | |
| 1. | Ammonium Laurate Stock | | |
| | Lauric Acid | 35.0 | |
| | Isopropanol (99%) | 14.7 | |
| | Sodium Hydrosulfite | 0.25 | |
| | Ethylenediamine tetra-acetate tetra sodium | 0.25 | |
| | Conc. Aqueous Ammonia (22%) | 12.8 | |
| | Water, deionized q.s. | | |
| | | 100.0 | |
| 2. | Shampoo Base | | |
| | Ammonium Laurate Stock (from 1 above) | 18.0 | |
| | Substituted oxazoline | 3.0 | |
| | Dicoco-dimethyl ammonium chloride | 0.5 | |
| | N-lauryl myristyl beta amino propionic acid | 0.5 | |
| | Lauroyl amide | 5.0 | |
| | Triethanolamine sulfonate | 8.0 | |
| | Triethanolamine salt of coconut oil fatty acids | 9.0 | |
| | Sodium lauryl sulfate (30%) | 9.0 | |
| | Oleic acid derivative of laurocyclo imidinium -1- ethoxyethionic acid -2- ethionic acid, di-sodium salt | 5.0 | |
| | Acetylated polyoxyethylene deriv. of lanolin | 1.0 | |
| | Propylene Glycol | 2.0 | |
| | Sodium Thiosulfate | 4.0 | |
| | Sodium Molybdate | 0.02 | |
| | Glycerine (99%) | 4.0 | |
| | KCl | 0.4 | |
| | Water, deionized q.s. | | |
| | | 100.0 | |
| | adjust pH to 10.3 with 28% Aqueous ammonia. | | |

| 3. | Final Composition | |
|---|---|---|
| | Hot Shampoo Base (from 2 above) | 100.0 |
| | p-Phenylene diamine | 0.072 |
| | p-Nitro-o-phenylene diamine | 0.032 |
| | o-Aminophenol (iron reduced) | 0.032 |
| | Pyrogallol | 0.24 |
| | Resorcinol | 0.20 |
| | o-Nitro-p-phenylene diamine | 0.48 |
| | o-Nitro-p-aminophenol | 0.16 |
| | p-Aminophenol | 0.32 |

Fill 92 parts by weight of Composition A into a pressure-tight container. Fill a collapsible container having a diameter smaller than the opening in the pressure-tight container with 100 parts by weight of Composition B. Insert collapsible container and affix valve means to communicate indidivually with the two compositions, the valve means being constructed such that actuation causes flow of Compositions A and B in the relative proportions of 1:1. Pressurize container with 8 parts by weight of a mixture of 50% dichlorodifluoromethane and 50% 1,2-dichloro-1,1,2,2-tetrafluoroethane. Actuation of the valve means results in the mixing of portions of the two compositions to yield a hair dye which is dispensed in a warmed state in a form ideally suited for hair dyeing purposes.

The following Example is illustrative of the use of a propellant system modified by the presence of pentane to impart delayed foaming of a hair dye composition after application to the hair.

EXAMPLE VI

The following compositions are utilized to prepare a package of the form illustrated in U.S. Pat. No. 2,973,883 for the purpose of dispensing a hair dye.

| A. | Hydrogen Peroxide Composition | Parts by Weight |
|---|---|---|
| | Acetophenetidin | .04 |
| | Polyoxyethylene (2) stearyl ether | 2.02 |
| | Polyoxyethylene (20) stearyl ether | 1.73 |
| | Cetyl alcohol | 1.0 |
| | Hydrogen Peroxide - 35% | 30.0 |
| | H₃PO₄ - 10% | 0.20 |
| | Water, deionized | q.s. |
| | | 100.0 |
| B. | Oxidation Hair Dye Composition | |
| | Oleic acid | 25.0 |
| | Polyoxyethylene (4) lauryl ether | 5.0 |
| | Polyoxyethylene (23) lauryl ether | 5.0 |
| | Ethoxylated (25) lanolin alcohol | 1.0 |
| | Lecithin | 1.25 |
| | Isopropanol (99%) | 10.0 |
| | Di-sodium ethylenediamine tetracetate | 0.1 |
| | Sodium sulfite anhydrous | 0.4 |
| | Sod. thiosulfate . 5H₂O | 4.06 |
| | Sod. molybdate . 2H₂O | 0.029 |
| | Pyro gallic acid | 0.25 |
| | Resorcinol | 0.20 |
| | Ortho amino phenol | 0.05 |
| | Para amino phenol | 0.40 |
| | Para phenylene diamine | 0.10 |
| | 2,4-diamino anisol | 0.60 |
| | para-nitro-ortho-phenylenediamine | 0.30 |
| | ortho-nitro-para-phenylenediamine | 0.70 |
| | ortho-nitro-para-aminophenol | 0.30 |
| | Propylene glycol | 4.0 |
| | NH₄OH 28% | 17.14 |
| | Perfume | 0.25 |
| | Potassium Chloride | 0.40 |
| | Water, Deionized | q.s. |

| -continued |
| --- |
| 100.000 |

Fill 100 parts by weight of Composition A into a pressure-tight container. Fill a collapsible container having a diameter smaller than the opening in the pressure-tight container with 100 parts by weight of Composition B. Insert collapsible container and affix valve means to communicate individually with the two compositions, the valve means being constructed such that actuation causes flow of Compositions A and B in the relative proportions of 1:1. Pressurize container with 16 parts by weight of a mixture of 50% pentane and 50% 1,2-dichloro-1,1,2,2-tetrafluoroethane. Actuation of the valve means results in the mixing of portions of the two compositions to yield a hair dye which is dispensed in a form ideally suited for hair dyeing purposes. Upon dispensing, the mixture is in the form of a thick, compact liquid which, after a time lag of 4 seconds, expands into a foam. The initial liquid state permits penetration of the composition to surround all hair on the head and the subsequent foam has good dimensional stability, thereby holding the composition to enable uniform dyeing action to take place.

The foregoing examples are illustrative of products within the scope of both the first and second product aspects of this invention. In all the examples, uniform proportioning of the two compositions is effected throughout the life of the package, even when the package is shaken prior to use. The following example is further supportive of the second product aspect of this invention in presenting a description of a dual-dispensed hot cleansing foam product:

EXAMPLE VII

| Composition A - Cleansing Foam Formulation | Parts by Weight |
| --- | --- |
| (i) Isopropyl lanolate | 0.50 |
| Lanolin oil | 0.50 |
| Ethylene oxide ether of lanolin alcohol | 4.50 |
| Light Mineral Oil | 5.00 |
| Stearic acid | 5.00 |
| Cetyl alcohol | 0.50 |
| (ii) Water | 49.55 |
| Triethanolamine | 4.00 |
| 45% KOH | 3.60 |
| Sodium Thiosulfate . 5H$_2$O | 5.60 |
| (iii) Perfume | 1.25 |
| | 80.00 |

| Composition B - Hydrogen Peroxide Formulation | |
| --- | --- |
| Ethoxylated protein hydrolysate | 8.00 |
| Hydrogen peroxide, 35% | 12.00 |

EXAMPLE VII-continued

| | 20.00 |
| --- | --- |

Composition A is prepared by heating, with stirring, sub-compositions (i) and (ii) to 95° C, cooling the mixture to room temperature and blending in the perfume.

Fill 20 parts by weight of Composition B into a pressure-tight container. Fill a collapsible container having a diameter smaller than the opening in the pressure-tight container with 80 parts by weight of Composition A. Insert collapsible container and affix valve means to communicate individually with the two compositions, the valve means being constructed such that actuation causes flow of Compositions A and B in the relative proportions of 4:1.

Pressurize container with 6 parts by weight of a mixture of 84% isobutane -16% propane. Actuation of the valve means results in dispensing of a warmed foam, ideally suited for facial cleansing purposes. Composition A is a highly foamable composition upon shaking. In spite of this property, uniform proportioning, as evidenced by uniform heat, results throughout the life of the package, brought about by the fact that the foamable composition is maintained throughout as a liquid column without head space.

It is to be understood that the invention is not to be limited to the exact compositions shown and described, as obvious modifications and equivalents will be apparent to one skilled in the art, and the invention is therefore to be limited only by the scope of the appended claims. The subject matter when the applicants regard as their invention is particularly pointed out and distinctly claimed as follows:

We claim:

1. A dispensing package having two compartments, one compartment containing one part of a two-part oxidative hair dye composition, the other compartment containing the other part of said composition, and means for mixing said parts including a pressure propellant to dispense said parts together, said one part comprising an aqueous solution containing an alkaline material selected from the group consisting of ammonium hydroxide, and short chain alkanolamines, said other part comprising an aqueous solution having a pH of about 3.75 containing from about 5.95 to about 10.5 percent hydrogen peroxide and about 0.1 percent phosphoric acid by weight, the amount of alkaline material in said first part and the amount of phosphoric acid in said other part being such as to provide a pH of about 8.5 to about 10.0 in the two-part composition immediately after mixing.

* * * * *